United States Patent
Appelt et al.

(10) Patent No.: US 7,221,448 B1
(45) Date of Patent: May 22, 2007

(54) TEST CELL FOR A NOBLE GAS POLARIZER

(75) Inventors: Stephan Appelt, Jülich (DE); Giovanni D'Orsaneo, Jülich (DE); Nadim Joni Shah, Linnich-Boslar (DE)

(73) Assignee: Forschungszentrum Julich GmbH, Julich (DE)

( * ) Notice: Subject to any disclaimer, the term of this patent is extended or adjusted under 35 U.S.C. 154(b) by 713 days.

(21) Appl. No.: 10/018,765

(22) PCT Filed: Jun. 7, 2000

(86) PCT No.: PCT/EP00/05251

§ 371 (c)(1),
(2), (4) Date: Mar. 28, 2002

(87) PCT Pub. No.: WO00/79244

PCT Pub. Date: Dec. 28, 2000

(30) Foreign Application Priority Data

Jun. 18, 1999 (DE) ............................. 199 27 788

(51) Int. Cl.
*G01N 1/10* (2006.01)
*G01N 21/01* (2006.01)
*C12Q 1/68* (2006.01)
*G02B 5/30* (2006.01)
*G02B 27/28* (2006.01)

(52) U.S. Cl. ..................... 356/246; 422/50; 422/52; 422/58; 422/83; 422/99; 422/102; 422/103; 250/200; 250/343; 250/373; 436/27; 436/28; 436/51; 436/300; 436/322; 436/364; 73/1.01; 73/1.02; 73/23.2; 359/483; 65/376; 65/404; 65/406; 65/407; 65/408

(58) Field of Classification Search .............. 422/50, 422/52, 58, 83, 99, 102, 103, 104; 436/27, 436/28, 51, 300, 322, 364; 73/1.01, 1.02, 73/23.2; 359/483; 65/376, 404, 406, 407, 65/408; 356/244, 246; 250/200, 343, 373

See application file for complete search history.

(56) References Cited

U.S. PATENT DOCUMENTS 4,523,740 A * 6/1985 Paitchell ............... 251/315.05

(Continued)

OTHER PUBLICATIONS

M.S. Rosen et al., "Polarized Xe Optical Pumping/spin Exchange and Delivery System for Magnetic Resonance Spectroscopy and Imaging Studies", *Review of Scientific Instruments*, American Institute of Physics, New York, US, vol. 70, No. 2, pp. 1546-1552, Feb. 1999.

(Continued)

*Primary Examiner*—Brian Sines
(74) *Attorney, Agent, or Firm*—Renner, Otto, Boisselle & Sklar, LLP

(57) ABSTRACT

The invention relates to a sample cell with a glass body comprising a gas inlet and a gas outlet and at least one orifice, a plane glass window is fused into the orifice, the shape and size of the window corresponds to the shape and size of the orifice, the orifice is limited by a rim, the rim is wider than the thickness of the window, the rim of the window is fused with the rim of the orifice.

Figure 1:
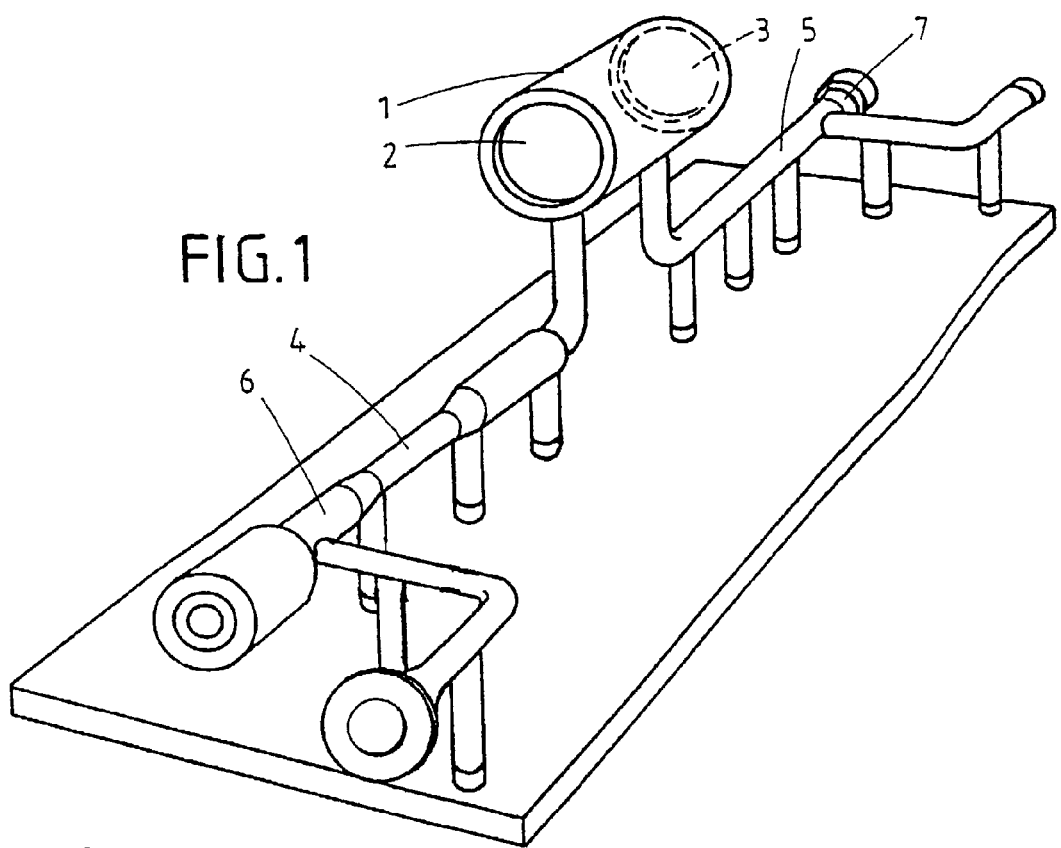

The invention further relates to a method of producing the sample cell. The window is inserted into the orifice. The rim of the orifice is heated several times from the exterior in such a way that the glass melts and a fused joint is formed between the window and the rim of the orifice.

The sample cell produced by the method has a particularly rigid joint between the window and the glass body. Therefore, this glass cell is able to withstand pressures above 10 bar and allows the passage of light without lens effects owing to its plane-parallel windows.

The sample cell is used in a polarizer for inert gas.

14 Claims, 1 Drawing Sheet

U.S. PATENT DOCUMENTS

| | | | |
|---|---|---|---|
| 4,616,927 A * | 10/1986 | Phillips et al. | 356/338 |
| 4,674,884 A * | 6/1987 | Heimel et al. | 356/440 |
| 4,907,884 A * | 3/1990 | Philips et al. | 356/336 |
| 4,980,551 A * | 12/1990 | Wong | 250/338.1 |
| 5,120,129 A * | 6/1992 | Farquharson et al. | 356/246 |
| 5,125,742 A * | 6/1992 | Wilks, Jr. | 356/246 |
| 5,414,508 A * | 5/1995 | Takahashi et al. | 356/246 |
| 5,414,723 A * | 5/1995 | Krapchev | 372/3 |
| 5,642,625 A | 7/1997 | Cates, Jr. et al. | |
| 5,785,729 A * | 7/1998 | Yokokawa et al. | 65/385 |
| 5,886,463 A * | 3/1999 | Damen et al. | 313/422 |
| 6,046,804 A * | 4/2000 | Kawamura et al. | 356/244 |
| 6,049,388 A * | 4/2000 | Masterson et al. | 356/426 |
| 6,368,560 B1 * | 4/2002 | Ostrander et al. | 422/91 |
| 6,433,482 B1 * | 8/2002 | Curry et al. | 313/637 |
| 6,603,555 B1 * | 8/2003 | Nanami et al. | 356/437 |

OTHER PUBLICATIONS

B. Driehuys et al., "High-volume Production of Laser-polarized 128XE", *Applied Physics Letters*, U.S. American Institute of Physics, New York, vol. 69, No. 12, pp. 1668-1670, Sep. 16, 1996.

* cited by examiner

TEST CELL FOR A NOBLE GAS POLARIZER

The invention relates to a sample cell for an inert gas polariser. The invention also relates to a method of producing the sample cell.

A sample cell for an inert gas polariser is known which consists of glass, a gas inlet and a gas outlet and through which the light of a laser is conveyed.

Recent developments in magnetic resonance tomography (MRT) and in magnetic resonance spectroscopy (NMR) with polarised inert gases have led to expectations of applications in medicine, physics and material sciences. High polarisation of nuclear spins may be achieved by optical pumping using alkali atoms, as demonstrated by the document Happer et al, Phys. Rev. A, 29, 3092 (1984). At present, rubidium is typically used in the presence of an inert gas and nitrogen. This enables nuclear spin polarisation of the inert gas xenon ($^{129}$Xe) of about 20 percent to be achieved. This nuclear spin polarisation is about 100,000 times greater than the equilibrium polarisation in clinical magnetic resonance tomographs. The associated drastic increase in the signal-to-noise ratio explains why possible new applications in medicine, science and technology are expected in future.

The term polarisation denotes the degree of orientation (ordering) of the spin of atomic nuclei or electrons. 100 percent polarisation denotes, for example, that all nuclei or electrons are oriented in the same manner. The polarisation of nuclei or electrons is associated with a magnetic moment.

Polarised xenon is, for example, inhaled by or injected into a person. The polarised xenon accumulates in the brain 10 to 15 seconds later. The distribution of the inert gas in the brain is detected by magnetic resonance tomography. The result is used for further analysis.

The choice of the inert gas depends on the application. $^{129}$xenon has a great chemical shift. If xenon, for example, is adsorbed on a surface, its resonant frequency changes significantly. Xenon also dissolves in fat-loving (i.e. lipophilic) liquids. Xenon is used when these properties are desired.

The inert gas helium barely dissolves in liquids. Therefore, the isotope $^{3}$helium is generally used when cavities are concerned. The human lung is an example of such a cavity.

Some inert gases have valuable properties different from those mentioned above. For example, the isotopes $^{83}$krypton, $^{21}$neon and $^{131}$xenon have a quadrupole moment which is of interest, for example, for experiments in basic research and in surface physics. However, these inert gases are very expensive so they are unsuitable for applications demanding relatively large amounts.

It is known from the document B. Driehuys et al, Appl. Phys. Lett. 69, 1668 (1996) to polarise inert gases in the following manner.

Circularly polarised light, i.e. light in which the angular momentum or the spin of the photons all point in the same direction is prepared using a laser. The angular momentum of the photons is transmitted to free electrons of alkali atoms. The spins of the alkali atom electrons therefore deviate greatly from the thermal equilibrium. The alkali atoms are therefore polarised. The polarisation of the electron spin is transmitted from an alkali atom to an inert gas atom by a collision between an alkali atom and an inert gas atom. Polarised inert gas is thus formed.

Alkali atoms are used as they have a great optical dipole moment which interacts with the light. Alkali atoms also have a respective free electron which prevents disadvantageous interactions between two and more electrons per atom.

Caesium would be a particularly suitable alkali atom and is superior to rubidium for achieving the aforementioned effects. At present, however, there are no lasers available with sufficiently high power, as required for the polarisation of xenon by means of caesium. However, it is expected that lasers with powers of 100 watts at the wavelength of caesium will be developed in future. Then, caesium will probably preferably be used for the polarisation of inert gases.

In the prior art, a gaseous mixture is conveyed slowly under a pressure typically of 7 to 10 bar through a cylindrical glass cell. The gaseous mixture consists of 98 percent of $^{4}$helium, one percent of nitrogen and one percent of xenon. The typical velocities of the gaseous mixture are a few ccm per second.

The gaseous mixture initially flows through a vessel (hereafter called "storage vessel") in which there is about one gram of rubidium. The storage vessel with the rubidium located therein is heated together with the adjoining glass cell to about 100 to 150 degrees Celsius. The rubidium is vaporised by providing these temperatures. The concentration of the vaporised rubidium atoms in the gaseous phase is determined by the temperature in the storage vessel. The gas stream conveys the vaporised rubidium atoms from the storage vessel into the cylindrical sample cell. A powerful circularly polarised laser (100 watt power in continuous operation) passes axially through the sample cell (also hereinafter called "glass cell") and optically pumps the rubidium atoms into a highly polarised state. The wavelength of the laser must be adapted to the optical absorption line of the rubidium atoms (Dl line). In other words, for optimum transmission of the polarisation of the light to an alkali atom, the frequency of the light must coincide with the resonant frequency of the optical crossover. The sample cell is located in a static magnetic field of a few 10 gauss which is generated by a coil (pair of Helmholtz coils). The direction of the magnetic field extends parallel to the cylinder axis of the sample cell or parallel to the beam direction of the laser. The magnetic field serves to guide the polarised alkali atoms. The rubidium atoms which are optically highly polarised by the light of the laser collide in the glass cell, inter alia with the xenon atoms, and transmit their high polarisation to the xenon atoms. On leaving the sample cell, the rubidium settles on the wall owing to the high melting point in comparison to the melting points of the other gases. The polarised xenon or the gaseous mixture is relayed from the sample cell into a freezeout unit. This consists of a glass flask of which the end is immersed in liquid nitrogen. The glass flask is also located in a magnetic field with a strength of 1,000 to 2,000 gauss. The highly polarised xenon gas settles on the internal glass wall of the freeze-out unit as ice when the glass wall is immersed into the liquid consisting of nitrogen. At the outlet of the freeze-out unit, the remaining gas (helium and nitrogen) is conveyed via a needle valve and finally discharged.

The flow rate in the entire arrangement can be controlled by the needle valve and can be measured using a measuring device. If there is an excessive increase in the flow rate, there is no time for transmission of polarisation from the rubidium atoms to the xenon atoms, so no polarisation is achieved. If the flow rate is too low, too much time elapses before the desired amount of highly polarised xenon freezes. In fact polarisation of the xenon atoms decreases again due to relaxation. Relaxation of the xenon atoms is markedly decelerated by the freezing and by the strong magnetic field to which the freeze-out unit is exposed. It is therefore necessary to freeze the inert gas as quickly as possible and with a minimum of loss after polarisation. Although relaxation cannot be avoided owing to freezing, there are still 1 to 2 hours at T=77 K before polarisation has diminished to such an extent that further use of the initially highly polarised gas is no longer possible.

A certain amount of energy is required to polarise a single free alkali atom. The energy required corresponds to the resonant frequency for raising the free electron of the alkali atom from the basic state into an excited state. For optimum transmission of the energy from a laser to the alkali atom, the frequency of the laser light must be adapted to the resonant frequency of the alkali atom. Lasers generally transmit their light within a specific frequency spectrum. This is not a single frequency but a distribution of frequencies. The available laser spectrum is characterised by the so-called line width. Alkali atoms are polarised most effectively if the line width of the laser coincides with the line width of the optical crossover of the alkali atom. The optical line width of an alkali atom is accordingly proportional to the pressure of the added $^4$helium laser (pressure broadening). In fact, the higher the pressure, the higher the number of collisions between an alkali atom and a collision partner such as helium.

The 100 watt strong laser used in the prior art is a glass fibre-coupled diode laser with a typical spectral width of 2 nanometers. At a gas pressure of 10 bar, the line width of the optical crossover of rubidium atoms is broadened to about 0.3 nanometers. Therefore, only a fraction of the laser light is used in existing rubidium/xenon polarisers in which expensive diode lasers with a typical line width of 2 nanometers are used for optical pumping. If the much cheaper diode lasers with a line width of 4 to 5 nm are used at 10 bar gas pressure, the efficiency is still much lower.

In a gaseous mixture according to the prior art, the partial pressures of helium are currently up to 10 bar. This is very high in comparison with the other partial pressures. In addition to the pressure broadening of the optical crossover of the alkali atom, the high partial pressure means that polarised atoms only rarely reach the sample wall of the glass cell and lose their polarisation there, for example due to interaction with paramagnetic centres. The likelihood that polarised atoms will disadvantageously collide with the cell wall decreases with increasing partial pressure.

In order to utilise the full power of the laser and at the same time to reduce disadvantageous relaxation effects due to collisions with the wall, helium pressure far above 30 bar would have to be employed.

The following should also be noted when putting together the gaseous mixture.

After absorbing a photon originating from the laser, an alkali atom such as rubidium is capable of emitting a photon due to fluorescence (fluorescence photon). If this fluorescence photon is captured by an adjacent polarised alkali atom, this capture leads to the depolarisation of the alkali atom. The nitrogen, used in the polarisation of inert gases, in the gaseous mixture suppresses ("quenches") this fluorescence radiation in order to reduce the aforementioned undesirable depolarisation. The nitrogen partial pressure is typically 0.1 bar in the prior art.

The heavy inert gas atoms, for example xenon atoms, cause marked relaxation in the polarisation of the alkali atoms during collisions with the alkali atoms. To maximise the polarisation of the alkali atoms during optical pumping, the partial pressure of the inert gases in the gaseous mixture has to be suitably low. Even with a xenon partial pressure in the gaseous mixture of only 0.1 bar, laser powers of 100 watts are required to achieve 70 percent polarisation of the alkali atoms in the entire sample volume.

Glass cells blown from one piece of glass are used in the prior art. In the past, there was no other way to produce a glass cell which was capable of withstanding the desired high pressures and at the same time ensured high optical quality. With the aforementioned production of the glass cell, the windows through which the laser light enters and issues are invariably curved or rounded. Undesirable disadvantageous lens effects occur during the ingress or egress of the laser light. The laser light is focussed or expanded. This considerably impairs the efficiency with which alkali atoms in the gaseous mixture of the glass cell are polarised.

A glass cell for the polarisation of inert gases is to satisfy the following requirements.

It must withstand a high pressure of at least 10 bar and be non-magnetic and resistant to alkali metals at temperatures of up to 200 degrees Celsius.

The glass cell should be adapted to be closed by valves. The valve heads or ring seals must withstand 200 degree Celsius in the presence of the gaseous mixture and must also be nonmagnetic and pressure-resistant. The influence of the valves on the polarisation of the inert gas should be as low as possible.

The surface in the interior of the cell should not have a destructive influence on xenon or rubidium polarisation. Therefore, there should be no paramagnetic or even ferromagnetic centres on the internal wall of the cell. The material making up the cell should be absolutely non-magnetic.

The laser light should be adapted to be propagated through the cell as far as possible without lens effects, i.e. in parallel.

The entry window of the cell should absorb as little as possible of the laser light. Otherwise, in particular the entry window will be excessively heated and ultimately destroyed.

The entry window should not be birefringent either at normal pressure or at high pressure. Otherwise, the circular polarisation of the laser would be destroyed or at least diminished.

An object of the invention is to provide a sample cell which is superior to the prior art in meeting these requirements.

The object of the invention is achieved by a glass cell having the features of the first claim. A method of producing the glass cell comprises the features of the independent claim. Advantageous developments emerge from the sub-claims.

The glass cell according to the claims comprises a glass body with an orifice. A plane glass window is inserted into the orifice. The shape and size of the window corresponds to the shape and size of the orifice. The orifice comprises a rim which is wider than the thickness of the window. This is to allow extensive contact between the window and the rim of the orifice. The rim of the window is fused with the rim of the orifice.

A glass cell comprising a flat entry window can thus be provided. This allows a parallel beam path through the window.

The glass body also comprises a gas inlet and a gas outlet.

The glass body has, in particular, the form of a cylinder. The plane window is then formed by a disc. The diameter of the disc corresponds to the internal diameter of the glass body. The disc is inserted a short distance into the cylinder. The internal wall of the cylinder then provides a large contact area which can be fused with the rim of the disc. This internal face then forms the rim of the orifice which is broader than the thickness of the window.

Advantageously, the two orifices of the cylinder are sealed by a respective plane window.

The cylinder further comprises a gas inlet and a gas outlet.

In order to join the window rigidly to the glass cell, the rim is heated several times, in particular to 1,400 to 1,500 degrees Celsius so the respective region is melted several times. If the glass body is a cylinder, it is heated from the exterior in order to fuse an inserted window with the cylinder.

A radius of 1 to 2 mm is created at the internal and external edge of the window owing to the repeated melting. As a result, the glass cell is pressure-resistant and at the same time has at least one plane entry window.

Advantageously, a window is ground prior to fitting and prior to fusion with the rim of the orifice of the glass body and is then cleaned with an acid, in particular with 15 percent hydrofluoric acid. In particular, the rim is ground cylindrically. These steps ensure a quite particularly durable joint with the rim of the orifice of the glass body.

Borosilicate glass is provided as material for the glass body or borofloate glass (borosilicate glass 3.3 ISO standard) for the window or windows. Both materials have the same coefficient of thermal expansion and may therefore be fused particularly well. Furthermore, both borosilicate glasses have few paramagnetic centres and are virtually not birefringent when pressure is applied, for example like quartz glass.

The glass body, for example the cylinder, typically has an internal diameter of 24 millimeters. The wall thickness is 5 millimeters or greater. A radius which joins the window to the glass body typically projects by 1 to 2 millimeters.

A glass cell of this type withstands a pressure of 15 bar.

Valves produced predominantly from glass are advantageously provided at the entrance and at the exit of the sample cell. If ring seals have been inserted for the glass valves, they consist of ethylene propylene. Ethylene propylene is resistant to alkalis and has no paramagnetic centres. Furthermore, the material absorbs virtually no inert gas.

No significant loss of polarisation was found immediately before and after this valve after NMR measurement of xenon polarisation.

The invention will be explained in more detail with reference to the following figures.

FIG. 1 shows the basic construction of the sample cell. The sample cell is composed of a cylinder 1 consisting of glass and two plane windows 2 and 3. The plane windows 2 and 3 are inserted a short distance into the respective ends of the cylinder. The windows 2 and 3 are rigidly joined to the cylinder 1. The gaseous mixture is initially conveyed into the sample cell and out again after polarisation. The tubes 4 and 5 may be sealed by valves 6 and 7. Inlet tube 4 has a portion of enlarged diameter between the valve 6 and the sample cell 1, 2, 3. This portion receives alkali metal which vaporises here and can then be transported into the sample cell.

Figure 2:
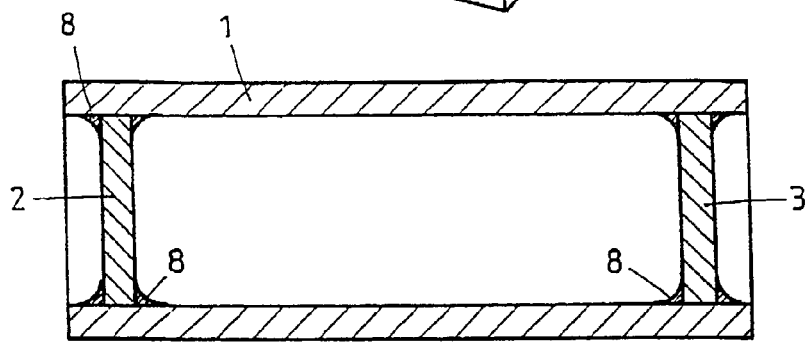

FIG. 2 is a cross-section of the sample cell. Entry window 2 and exit window 3 are inserted a short distance into the cylinder 1. The windows 2 and 3 have been joined to the cylinder 1 by repeated melting. The radii 8 form a fused joint between the plane windows 2 and 3 and the cylinder 1. The radii 8 are located on either side of a respective window 2 and 3 and adjoin the cylinder 1. The cylinder 1 consists of borosilicate glass. The windows consist of borofloate glass. The cylinder wall is 5 mm thick. The windows also have a wall thickness of 5 millimeters. The external diameter of the cylinder is about 35 to 40 mm.

Borofloate glass and borosilicate glass have the same coefficients of thermal expansion. The windows therefore fuse particularly well with the cylinder. A very pressure-resistant cell then exists, which even withstands pressures of 15 bar.

Figure 3:
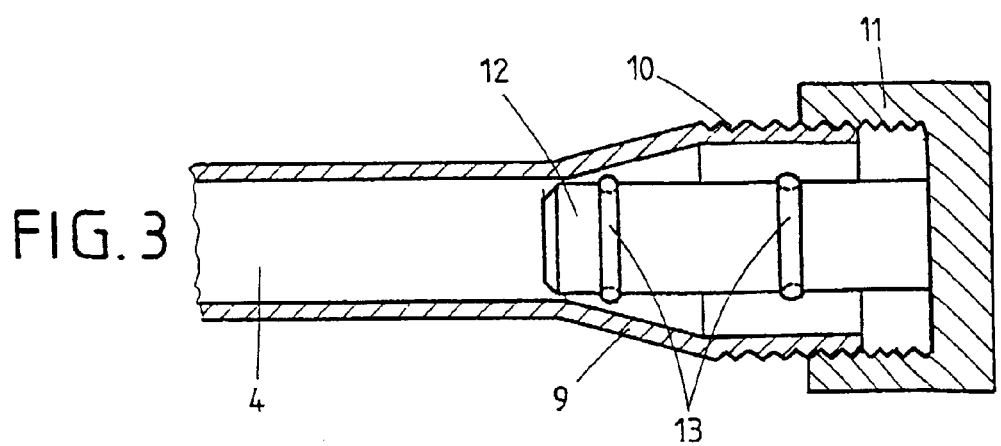

FIG. 3 is a cross-section through a valve 6 or 7. The end of a line 4 (tube) consisting of glass opens into a funnel 9. A thread 10 adjoins the funnel. A cap 11 composed of plastics material is screwed onto the thread 10. The cap 11 has a corresponding internal thread. A bolt 12 consisting of glass is fastened centrally internally on the cap 11. The bolt 12 penetrates into the funnel 9. The bolt 12 comprises two grooves containing O-rings 13. The O-rings 13 consist of ethylenepropylene. A branching tube located at the upper rim with the large diameter of the funnel 9 is not shown. An intermediate length of pipe, not shown, from which a tube branches may also be provided between funnel 9 and thread 10.

Once the cap 11 is screwed in, the leading O-ring produces a tight seal with the funnel 9. The valve is then closed.

The bolt 12 can have a greater external diameter than the internal diameter of the tube 4 and, at the end facing the funnel, a tapering portion which opens into the funnel. This portion acts as a counterpart to the funnel. An O-ring is provided at the tapering portion in such a way that the tapering portion ends tight against the funnel 9 when the bolt 12 has been moved sufficiently far in the direction of the funnel by screwing of the cap 11. The aforementioned high pressures are possible, in particular, with this embodiment.

The invention claimed is:

1. A sample cell comprising a glass body including a gas inlet, a gas outlet and at least one orifice formed by a tubular portion of the glass body; and a plane glass window closing the orifice, the shape and size of the window corresponding to the shape and size of the orifice, the glass window being joined at its outer rim to the interior surface of the tubular portion by a fused joint, and the tubular portion projecting outwardly beyond an outer face of the glass window to accommodate an axially outer portion of the fused joint that projects outwardly beyond the outer face of the glass window.

2. A sample cell according to claim 1, wherein the glass body has the form of a cylinder, the plane window is formed by a disc, and the disc is inserted into the glass body at one end of the cylinder and spaced axially inwardly of the end of the cylinder.

3. A sample cell according to claim 1, wherein the sample cell comprises two plane windows which are arranged parallel to one another.

4. A sample cell according to claim 1, wherein the fused joint includes two projecting radii of at least one millimeter formed on respective sides of the window as a result of the window being fused to the rim of the orifice, one such radii corresponding to the axially outer portion of the fused joint.

5. A sample cell according to claim 1, wherein the glass body is made of borosilicate glass and the window is made of borofloate glass.

6. A sample cell according to claim 1, wherein the wall of the glass body is at least 5 mm thick.

7. A sample cell according to claim 1, wherein the external diameter of the glass body is between 20 and 100 millimeters.

8. A sample cell according to claim 1, and valves connected to the gas inlet and gas outlet, the valves being made from glass and including ring seals made of ethylene propylene at an entrance and exit for a gas.

9. A method of producing a sample cell comprising:

inserting a plane glass window into an orifice of a glass body that further has an inlet and an outlet, the circumference of the window corresponding to the circumference of the orifice and the orifice being formed by a tubular portion of the glass body, and heating the tubular portion from the exterior at least twice in such a way that the glass in the vicinity of the tubular portion melts, creating a fused joint between the window at its rim and the tubular portion, and wherein the window is positioned in the tubular portion such that a portion of the tubular portion projects outwardly beyond an outer face of the window to accommodate an axially outer portion of the fused joint that projects outwardly beyond the outer face of the glass window.

10. A method according to claim 9, in which the rim of the window is ground prior to insertion and prior to fusion with the tubular portion of the glass body.

11. A method of using a sample cell according to claim 1, comprising passing a gas through the sample cell at pressures of at least 10 bar.

12. A sample cell according to claim 1, wherein the glass body has an external diameter between 35 and 40 millimeters.

13. A method according to claim 10, wherein the an interior surface of the tubular portion is ground cylindrically and is then cleaned with an acid.

14. A method according to claim 13, wherein the acid is hydrofluoric acid.

* * * * *